United States Patent [19]

Gutman

[11] 4,016,266

[45] Apr. 5, 1977

[54] N-ALKYLTHIOMETHYLACETAMIDEPHOS-PHORODITHIOATE INSECTICIDES

[75] Inventor: Arnold D. Gutman, Berkeley, Calif.

[73] Assignee: Stauffer Chemical Company, Westport, Conn.

[22] Filed: June 2, 1975

[21] Appl. No.: 582,964

[52] U.S. Cl. .............................. 424/211; 260/943
[51] Int. Cl.² .................. A01N 9/36; C07F 9/165
[58] Field of Search .................... 260/943; 424/211

[56] References Cited

UNITED STATES PATENTS

| | | | |
|---|---|---|---|
| 3,013,940 | 12/1961 | Fusco et al. | 260/943X |
| 3,057,774 | 10/1962 | Baker et al. | 260/943 X |
| 3,106,510 | 10/1963 | Szabo et al. | 260/943 X |

FOREIGN PATENTS OR APPLICATIONS 1,016,666   1/1966   United Kingdom ............... 260/943

*Primary Examiner*—Anton H. Sutto
*Attorney, Agent, or Firm*—Joel G. Ackerman

[57] ABSTRACT

Novel compounds having the formula

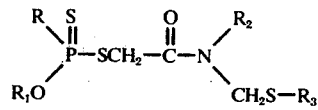

in which R is lower alkyl or alkoxy; $R_1$ and $R_2$ are lower alkyl; and $R_3$ is lower alkyl, p-chlorophenyl or

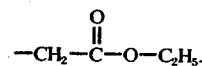

The compounds have utility as insecticides and miticides.

28 Claims, No Drawings

N-ALKYLTHIOMETHYLACETAMIDEPHOSPHORODITHIOATE INSECTICIDES

SUMMARY OF THE INVENTION AND PRIOR ART

The present invention relates to novel N-alkylthiomethylacetamidephosphorodithioate, particularly such compounds having N,N-disubstitution therein. More specifically, this invention relates to compounds of the formula

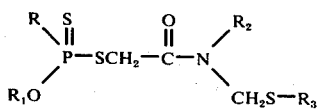

in which R is lower alkyl or lower alkoxy; $R_1$ and $R_2$ are lower alkyl; and $R_3$ is lower alkyl, p-chlorophenyl or

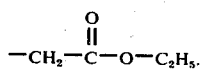

By the terms "lower alkyl" and "lower alkoxy" are meant such groups having from 1 to 6, preferably from 1 to 4, carbon atoms, for example, methyl, ethyl, n-propyl, n-butyl, sec.-butyl, tert-butyl, methoxy, ethoxy and the like.

Some compounds having a somewhat similar structure, but being secondary amines (i.e. $R_2$ is hydrogen) are shown in U.S. Pat. Nos. 3,013,940 and 3,106,510.

The compounds of the present invention, as will appear from the data which follows, have utility as insecticides and miticides. These compounds have been found to show particular utility in controlling aphids.

One preferred embodiment of the invention comprises compounds according to the above formula in which R is ethyl and, particularly in which R and $R_1$ are both ethyl.

In another preferred embodiment of the invention, the compounds of the above formula are those in which $R_2$ is methyl or ethyl, particularly in which $R_2$ is methyl, and most particularly in which both $R_2$ and $R_3$ are methyl.

In yet another preferred embodiment of the invention, the compounds of the above formula have R being methoxy, and $R_1$ and $R_2$ methyl.

When R is methoxy and $R_1$ is methyl, preferably at least one, and most preferably both, of $R_2$ and $R_3$ is methyl or ethyl.

In another aspect, the invention also relates to a process or method for controlling insects by applying to the insect or the habitat thereof an insecticidally effective amount of a compound having the formula

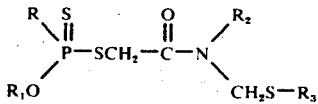

in which R is lower alkyl, or lower alkoxy; $R_1$ and $R_2$ are lower alkoxy; and $R_3$ is lower alkyl, p-chlorophenyl or

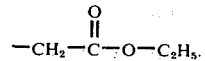

Preferred methods of controlling insects involve the use of the preferred types of compounds mentioned above.

DETAILED DESCRIPTION OF THE INVENTION

In general, the compounds of the present invention are prepared by reacting a substituted 1,3,5-hexahydro S-triazine with a mercaptan and gaseous hydrogen chloride, and then reacting the resultant alkylthiomethylamine salt in turn with chloroacetyl chloride and a phosphate salt to produce the desired compound.

The following examples demonstrate the preparation of compounds of the present invention.

EXAMPLE 1

Preparation of Starting Materials 350 ml of acetonitrile and 20 g (0.155 mole) of 1,3,5-trimethylhexahydro S-triazine were charged to a 1-liter, three-neck, round-bottom flask equipped with a stirrer, thermometer, and a gas-inlet tube. The solution was stirred and cooled to −30° C. with a dry-ice/acetone bath. 18.6 g (0.52 mole) of HCl gas were added at −30° C., followed by the addition of 24 g (0.51 mole) of methylmercaptan gas. The reaction mass was allowed to warm to room temperature and stand overnight (removed under vacuum). The residue was triturated with 500 ml of cold diethylether and the white solid product (N-methyl-N-methylthiomethylamine hydrochloride) was collected by filtration and dried in a desiccator. This compound (Compound I) was obtained in a yield of 44.3 g (75.3% of theory).

11.3 g (0.1 mole) of chloroacetylchloride, 300 ml of acetonitrile and 12.6 g (0.1 mole) of Compound I, prepared by the above procedure, were combined in a 500 ml, three-neck flask fitted with a stirrer, thermometer and dropping funnel. The mixture was stirred and cooled to 0° C. 20.2 g (0.2 mole) of triethylamine were added over a period of 30 minutes while the reaction temperature was maintained at 0°-5° C. After the addition was complete, the mixture was stirred at room temperature for one hour. The reaction mass was filtered and stripped under vacuum. The residue was taken up in 200 ml of benzene and washed with 100 ml of water. The benzene phase was dried with anhydrous magnesium and evaporated under vacuum to yield 11.9 g (71% of theory) of N-methyl-N-methylthiomethylchloroacetamide (Compound II), $n_D^{30}$ − 1.4220.

EXAMPLE 2

N-methyl-N-methylthiomethyl)-O,O-dimethylphosphorodithionylacetamide (Compound 14 hereinbelow) was prepared as follows:

3.5 g (0.022 mole) of O,O-dimethyldithiophosphoric acid were combined with 3 g of potassium carbonate in 50 ml of acetone. The mixture was stirred until the salt was obtained. The acetone was then decanted into a 200 ml round-bottom flask containing 3.2 g (0.02 mole) of Compound II in 50 ml of acetone. After standing at room temperature for 1 hour, the mixture was poured into 300 ml of benzene and washed with two 200 ml portions of water. The benzene phase was then dried with anhydrous magnesium sulfate and evaporated under vacuum to yield 4.1 g (72% of theory) of the desired compound, $n_D^{30}$ — 1.5000.

EXAMPLE 3

N-methyl-N-methylthiomethyl-O,O--diethylphosphorodithionylacetamide (Compound 15 hereinbelow):

This compound was prepared in the same manner as Example 2 from 2.5 g (0.015 mole) of Compound II, 3.15 g (0.017 mole) of O,O-diethyldithiophosphoric acid and 3 g of potassium carbonate. There were obtained 4.0 g (84% of theory) of the desired compound, $n_D^{30}$ — 1.5395.

EXAMPLE 4

N-methyl-N-methylthiomethyl-α-O-ethyl, -ethyl-phosphonodithioylacetamide (Compound 16 hereinbelow):

This was prepared in the same manner as Example 2 from 2.5 g (0.015 mole) of Compound II, 2.9 g (0.017 mole) of O-ethyl, ethyldithioylphosphonic acid and 3 g of potassium carbonate. There was obtained 4.0 g of the desired compound (88% of theory), $n_D^{30}$ — 1.5560.

EXAMPLE 5

N-methyl-N-t-butylthiomethyl-α-(O-ethyl, ethyl-phosphorodithioyl)acetamide (Compound 23 hereinbelow):

This compound was prepared in the same manner as Example 2 from 3.13 g (0.015 mole) of N-methyl-N-t-butylthiomethylchloroacetamide, 3.0 g (0.016 mole) of O,O-diethyldithiophosphoric acid and 3 g potassium carbonate. 4.2 g of the desired compound were obtained (87.5% of theory), $n_D^{30}$ — 1.5285.

The following table is a list of some compounds of the present invention which may be prepared according to the above procedures.

TABLE I

| Compound No. | R | $R_1$ | $R_2$ | $R_3$ | $N_D^{30}$ |
|---|---|---|---|---|---|
| 1 | $CH_3O$ | $CH_3$ | $n-C_3H_7$ | $n-C_3H_7$ | 1.5238 |
| 2 | $C_2H_5O$ | $C_2H_5$ | $n-C_3H_7$ | $n-C_3H_7$ | 1.5202 |
| 3 | $C_2H_5O$ | $C_2H_5$ | $n-C_3H_7$ | $C_2H_5$ | 1.5213 |
| 4 | $CH_3O$ | $CH_3$ | $n-C_3H_7$ | $C_2H_5$ | 1.5202 |
| 5 | $C_2H_5O$ | $C_2H_5$ | $n-C_3H_7$ | $CH_3$ | 1.5298 |
| 6 | $CH_3O$ | $CH_3$ | $n-C_3H_7$ | $CH_3$ | 1.5272 |
| 7 | $CH_3O$ | $CH_3$ | $CH_3$ | $C_2H_5$ | 1.5400 |
| 8 | $C_2H_5O$ | $C_2H_5$ | $CH_3$ | $C_2H_5$ | 1.5352 |
| 9 | $C_2H_5O$ | $C_2H_5$ | $CH_3$ | p-chlorophenyl | 1.5675 |
| 10 | $CH_3O$ | $CH_3$ | $CH_3$ | p-chlorophenyl | 1.5672 |
| 11 | $CH_3O$ | $CH_3$ | $s-C_4H_9$ | $C_2H_5$ | 1.5272 |
| 12 | $C_2H_5O$ | $C_2H_5$ | $s-C_4H_9$ | $C_2H_5$ | 1.5210 |
| 13 | $C_2H_5$ | $C_2H_5$ | $s-C_4H_9$ | $C_2H_5$ | 1.5328 |
| 14 | $CH_3O$ | $CH_3$ | $CH_3$ | $CH_3$ | 1.5500 |
| 15 | $C_2H_5O$ | $C_2H_5$ | $CH_3$ | $CH_3$ | 1.5395 |
| 16 | $C_2H_5$ | $C_2H_5$ | $CH_3$ | $CH_3$ | 1.5560 |
| 17 | $C_2H_5O$ | $C_2H_5$ | $C_2H_5$ | $CH_2COOC_2H_5$ | 1.5185 |
| 18 | $CH_3O$ | $CH_3$ | $C_2H_5$ | $CH_2COOC_2H_5$ | 1.5180 |
| 19 | $C_2H_5$ | $C_2H_5$ | $C_2H_5$ | $CH_2COOC_2H_5$ | 1.5354 |
| 20 | $C_2H_5O$ | $C_2H_5$ | $C_2H_5$ | $t-C_4H_9$ | 1.5203 |
| 21 | $CH_3O$ | $CH_3$ | $C_2H_5$ | $t-C_4H_9$ | 1.5313 |
| 22 | $C_2H_5$ | $C_2H_5$ | $C_2H_5$ | $t-C_4H_9$ | 1.5334 |
| 23 | $C_2H_5O$ | $C_2H_5$ | $CH_3$ | $t-C_4H_9$ | 1.5285 |
| 24 | $CH_3O$ | $CH_3$ | $CH_3$ | $t-C_4H_9$ | 1.5383 |

The following tests illustrate the insecticidal and acaricidal activity of the compound of this invention.

Insecticidal Evaluation Tests

The following insect species were used in evaluation tests for insecticidal activity:

1. Housefly (HF) — *Musca domestica* (Linn.)
2. German Roach (GR) — *Blatella germanica* (Linn.)
3. Salt-marsh Caterpillar (SMC) — *Estigmene acrea* (Drury)
4. Lygus Bug (LB) — *Lygus hesperus* (Knight)
5. Bean Aphid (BA) — *Aphis fabae* (Scop.)
6. Green Peach Aphid (GPA) — *Myzus persicae* (Sulzer)

The insecticidal evaluation tests were conducted as follows:

Housefly

Test compounds were diluted in acetone and aliquots pipetted onto the bottom of 55 × 15 mm aluminum dishes. To insure even spreading of the chemical on the bottom of the dishes, 1 ml of acetone containing 0.02% peanut oil was also added to each dish. After all solvents had evaporated, the dishes were placed in circular cardboard cages containing 25 female houseflies, 1 to 2 days old. The cages were covered on the bottom with cellophane and on the top with tulle netting, and each contained a sugar-water saturated cotton plug for maintenance of the flies. Mortality was recorded after 48 hours. Test levels ranged from 100 μg/25 female houseflies down to that at which approximately 50% mortality occurred. The LD-50 values are expressed below in Table II under the heading "HF", in terms of μg of the test compound per 25 female flies.

German Cockroach

Test compounds were diluted in a 50—50 acetone-water solution. 2 cc of the solution were sprayed through a DeVilbiss type EGA hand spray gun into circular cardboard cages containing 10 one-month-old German cockroach nymphs. The test cages were covered on the bottom with cellophane and on the top with tulle netting. Percent mortality was recorded 7 days later. Test concentrations ranged from 0.1% down to that at which approximately 50% mortality occurred. LD-50 values are expressed below in Table II under the heading "GR" in terms of percent of the test compound in the sprayed solution.

Salt-Marsh Caterpillar

Test compounds were diluted in a 50—50 acetone-water solution. Sections of curly dock (*Rumex crispus*) leaves, approximately 1 × 1.5 inches, were immersed in the test solution for 2–3 seconds and placed on a wire screen to dry. The dried leaves were placed in petri dishes containing a moistened piece of filter paper and infested with 5 second-instar salt-marsh larvae. Mortality of the larvae was recorded 48 hours later, and a piece of synthetic media was added to dishes containing survivors. These were then held for 5 additional days to observe for any delayed effects of the test chemicals.

Test concentrations ranged from 0.05% down to that at which approximately 50% mortality occurred. LD-50 values are expressed below in Table II under the heading "SMC" in terms of percent of the test compound in the solution.

Lygus Bug

Test compounds were diluted in a 50—50 acetone-water solution. 2 cc of the solution were sprayed through a DeVilbiss type EGA hand spray gun into circular cardboard cages containing 1 string bean pod and 10 adult lygus bugs. The test cages were covered on the bottom with cellophane and on the top with tulle netting. Percent mortality was recorded 48 hours later. Test concentrations ranged from 0.05% down to that at which approximately 50% mortality occurred. LD-50 values are expressed below in Table II under the heading "LB" in terms of percent of the test compound in the sprayed solution.

Black Bean Aphid

Nasturtium plants (*Tropaeolum sp.*), approximately 5 cm tall, were transplanted into sandy loam soil in 3-inch clay pots and infested with 25–50 black bean aphids of mixed ages. 24 Hours later, they were sprayed, to the point of runoff, with 50—50 acetone-water solutions of the test chemicals. Treated plants were held in the greenhouse and mortality was recorded after 7 days. Test concentrations ranged from 0.05% down to that at which 50% mortality occurred. LD-50 values are expressed below in Table II under the heading "BA" in terms of percent of the test compound in the sprayed solution.

Green Peach Aphid

Radish plants (*Rhaphanus sativus*), approximately 2 cm tall, were transplanted into sandy loam soil in 3-inch pots and infested with 25–50 green peach aphids of mixed ages. 24 hours later, they were sprayed, to the point of runoff, with 50—50 acetone-water solutions of the test chemicals. Treated plants were held in the greenhouse and mortality was recorded after 48 hours. Test concentrations ranged from 0.05% down to that at which approximately 50% mortality occurred. LD-50 values are expressed below in Table II under the heading "GPA" in terms of percent of the test compound of the sprayed solution.

Acaricidal Evaluation Test

The two-spotted mite (2SM), *Tetranychus urticae* (Koch), was employed in tests for miticides. The test procedure was as follows:

Pinto bean plants (*Phaseolus sp.*) approximately 10 cm tall, were transplanted into sandy loam soil in 3-inch clay pots and thoroughly infested with two-spotted mites of mixed ages and sexes. 24 hours later, the infested plants were inverted and dipped for 2–3 seconds in 50—50 acetone-water solutions of the test chemicals. Treated plants were held in the greenhouse, and 7 days later mortality was determined for both the adult mites and the nymphs hatching from eggs which were on the plants at the time of treatment. Test concentrations ranged from 0.05% down to that at which 50% mortality occurred. LD-50 values are expressed below in Table II under the headings "2SM-PE" (i.e., post-embryonic) and "2SM-Eggs," in terms of percent concentration of the test compound in the solution.

Systematic Evaluation Test

This test evaluates the root absorption and upward translocation of the candidate systemic compound. The two-spotted mite (2SM) *Tetranychus urticae*, (Koch) and the Bean Aphid (BA) — *Aphis fabae* (Scop.) were employed in the test for systemic activity. Tests were conducted as follows:

Two-Spotted Mite

Test chemicls were dissolved in acetone and aliquots diluted in 200 cc of water in glass bottles. 2 pinto bean plants (*Phaseolus sp.*), with expanded primary leaves, were supported in each bottle by cotton plugs, so that their roots and stems were immersed in the treated water. The plants were then infested with 75–100 two-spotted mites of various ages and sexes. One week later the mortality of the adult mites and nymphs was recorded. Test concentrations in the medium ranged from 10 ppm down to that at which 50% mortality occurred.

Black Bean Aphid

Test chemicals were diluted in acetone and aliquots thoroughly mixed into 500 grams of dry, sandy loam soil. The treated soil was placed in a pint-sized carton and a nasturtium plant (*Tropaeolum sp.*) approximately 5 cm tall was transplanted into each carton. The plants were then infested with approximately 25 black bean aphids of mixed ages and placed in the greenhouse. 7 Days later mortality was recorded, and plants which showed 100% mortality at 1 ppm were reinfested with aphids. This procedure was repeated weekly until all control was lost. Test concentrations ranged from 10 ppm down to that at which approximately 50% mortality occurred. LD-50 values are expressed below in Table II under the headings "2SM-Syst" and "BA(-syst)" respectively, in terms of percent concentration of the test compound.

TABLE II

| Compound No. | HF μg | GR % | LB % | BA % | BA(syst) ppm | GPA % | SMC % | 2-SM PE % | 2-SM Eggs % | 2-SM Syst ppm |
|---|---|---|---|---|---|---|---|---|---|---|
| 1 | 75 | >.1 | .05 | .001 | >10 | >.05 | >.05 | >.05 | >.05 | |
| 2 | 30 | >.1 | >.05 | .003 | >10 | | .05 | <.05 | <.05 | 10 |
| 3 | 35 | >.1 | .05 | .003 | 8 | | >.05 | >.05 | >.05 | |
| 4 | >100 | >.1 | >.05 | .008 | >10 | | >.05 | >.05 | >.05 | |
| 5 | 30 | >.1 | >.05 | .0003 | 3 | .005 | .05 | <.05 | <.05 | 3 |
| 6 | 50 | >.1 | >.05 | .001 | .8 | .05 | >.05 | <.05 | <.05 | 3 |
| 7 | 30 | >.1 | .005 | .0005 | 1 | .005 | >.05 | .003 | .008 | .8 |
| 8 | 30 | >.1 | .008 | .0001 | 1 | .001 | >.05 | <.05 | <.05 | 3 |
| 9 | 20 | >.1 | >.05 | .001 | 3 | .01 | >.05 | <.05 | <.05 | >10 |
| 10 | 100 | >.1 | >.05 | .005 | >10 | | >.05 | <.05 | <.05 | >10 |
| 11 | >100 | >.1 | >.05 | .003 | 10 | >.05 | >.05 | <.05 | <.05 | 5 |
| 12 | 35 | >.1 | .003 | .001 | >10 | .01 | >.05 | <.05 | <.05 | 3 |
| 13 | 35 | >.1 | .001 | .0003 | 3 | .003 | .05 | <.05 | <.05 | 3 |
| 14 | 30 | >.1 | .001 | .0003 | .5 | | >.05 | | | .5 |
| 15 | 25 | >.1 | .003 | .0003 | .5 | .005 | >.05 | | | 1 |
| 16 | 25 | >.1 | .0008 | .0003 | .5 | .001 | >.05 | .0005 | .001 | .5 |
| 17 | 50 | >.1 | >.03 | .001 | 5 | .03 | >.05 | >.05 | >.05 | |
| 18 | >100 | >.1 | >.03 | .005 | >10 | | >.05 | >.05 | >.05 | |
| 19 | 30 | >.1 | >.03 | .0008 | 1 | .001 | >.05 | <.05 | <.05 | >10 |
| 20 | 45 | >.1 | >.03 | .0008 | 3 | .03 | >.05 | <.05 | <.05 | >10 |
| 21 | >100 | >.1 | >.03 | .003 | 5 | .01 | >.05 | <.05 | <.05 | 10 |
| 22 | 30 | >.1 | .005 | .0008 | 1 | .001 | .05 | <.05 | <.05 | 8 |
| 23 | 75 | >.1 | >.05 | .0005 | 1 | .01 | >.05 | <.05 | <.05 | >10 |
| 24 | 40 | >.1 | .01 | .003 | .8 | >.05 | >.05 | <.05 | <.05 | >10 |

As those in the art are well aware, various techniques are available for incorporating the active component or toxicant in suitable pesticidal compositions. Thus, the pesticidal compositions can be conveniently prepared in the form of liquid or solids, the latter preferably as homogeneous free-flowing dusts commonly formulated by admixing the active component with finely divided solids or carriers as exemplified by talc, natural clays, diatomaceous earth, various flours, such as walnut shell, wheat, soya bean, cottonseed and so forth.

Liquid compositions are also useful and normally comprise a dispersion of the toxicant in a liquid media, although it may be convenient to dissolve the toxicant directly in a solvent such as kerosene, fuel oil, xylene, alkylated napthalenes or the like and use such organic solutions directly. However, the more common procedure is to employ dispersions of the toxicant in an aqueous media and such compositions may be produced by forming a concentrated solution of the toxicant in a suitable organic solvent followed by dispersion in water, usually with the aid of surface active agents. The latter, which may be the anionic, cationic, or nonionic types, are exemplified by sodium stearate, potassium oleate and other alkaline metal soaps and detergents such as sodium lauryl sulfate, sodium naphthalene sulfonate, sodium alkyl napthalene sulfonates, methyl cellulose, fatty alcohol ethers, polyglycol fatty acid esters and other polyoxyethylene surface active agents. The proportion of these agents commonly comprises 0.1–20% by weight of the pesticidal compositions although the proportion is not critical and may be varied to suit any particular situation.

What is claimed is:

1. A method for controlling insects comprising applying to the insects or the habitat thereof an insecticidally effective amount of a compound having the formula

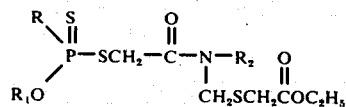

in which R is lower alkyl or lower alkoxy and $R_1$ and $R_2$ are lower alkyl.

2. A method according to claim 1 in which R is lower alkyl.
3. A method according to claim 2 in which R is ethyl.
4. A method according to claim 1 in which R is lower alkoxy.
5. A method according to claim 4 in which R is ethoxy.
6. A method according to claim 4 in which R is methoxy.
7. A method according to claim 1 in which $R_1$ is methyl.
8. A method according to claim 1 in which $R_1$ is ethyl.
9. A method according to claim 1 in which R and $R_1$ are lower alkyl.
10. A method according to claim 9 in which R is ethyl.
11. A method according to claim 9 in which R and $R_1$ are ethyl.
12. A method according to claim 1 in which $R_2$ is ethyl.
13. An insecticidal composition comprising: (a) an insecticidally effective amount of a compound having the formula

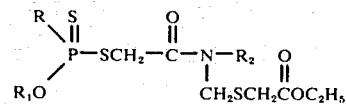

in which R is lower alkyl or lower alkoxy and $R_1$ and $R_2$ are lower alkyl; and (b) an inert carrier.

14. A compound having the formula

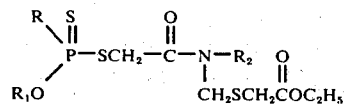

in which R is lower alkyl or lower alkoxy and $R_1$ and $R_2$ are lower alkyl.

15. A compound according to claim 14 in which R is lower alkyl.
16. A compound according to claim 15 in which R is ethyl.
17. A compound according to claim 14 in which R is lower akloxy.
18. A compound according to claim 17 in which R is ethoxy.
19. A compound according to claim 17 in which R is methoxy.
20. A compound according to claim 14 in which $R_1$ is methyl.
21. A compound according to claim 14 in which $R_1$ is ethyl.
22. A compound according to claim 14 in which R and $R_1$ are lower alkyl.
23. A compound according to claim 22 in which R is ethyl.
24. A compound according to claim 22 in which R and $R_1$ are ethyl.
25. A compound according to claim 14 in which $R_2$ is ethyl.
26. A compound according to claim 14 in which R is ethoxy; $R_1$ is ethyl and $R_2$ is ethyl.
27. A compound according to claim 14 in which R is methoxy, $R_1$ is methyl and $R_2$ is ethyl.
28. A compound according to claim 14 in which R, $R_1$ and $R_2$ are all ethyl.

* * * * *